United States Patent
Zhu et al.

(10) Patent No.: US 10,872,516 B2
(45) Date of Patent: Dec. 22, 2020

(54) TIMING REMINDING METHOD AND REMINDING APPARATUS FOR HEIGHT-ADJUSTABLE TABLE

(71) Applicant: SHENZHEN MINICUTE TECHNOLOGY CO. LTD., Shenzhen (CN)

(72) Inventors: Wenbin Zhu, Shenzhen (CN); Yifei Xie, Shenzhen (CN)

(73) Assignee: Shenzhen Minicute Technology Co. Ltd., Shenzhen (CN)

( * ) Notice: Subject to any disclaimer, the term of this patent is extended or adjusted under 35 U.S.C. 154(b) by 0 days.

(21) Appl. No.: 16/344,265

(22) PCT Filed: Oct. 7, 2017

(86) PCT No.: PCT/CN2017/092409
§ 371 (c)(1),
(2) Date: Apr. 23, 2019

(87) PCT Pub. No.: WO2018/076786
PCT Pub. Date: May 3, 2018

(65) Prior Publication Data
US 2019/0266879 A1    Aug. 29, 2019

(30) Foreign Application Priority Data
Oct. 24, 2016  (CN) .......................... 2016 1 0932321

(51) Int. Cl.
*G08B 21/24*    (2006.01)
*A47B 21/02*    (2006.01)
(Continued)

(52) U.S. Cl.
CPC ............... *G08B 21/24* (2013.01); *A47B 9/00* (2013.01); *A47B 13/00* (2013.01); *A47B 21/02* (2013.01);
(Continued)

(58) Field of Classification Search
CPC ...................................................... G08B 21/24
See application file for complete search history.

(56) References Cited

U.S. PATENT DOCUMENTS 3,670,457 A * 6/1972 Berkholcs ............... B24B 47/04
                                                    451/213
9,038,549 B1 * 5/2015 Zebarjad .................. A47B 9/02
                                                    108/147
(Continued)

FOREIGN PATENT DOCUMENTS

CN        105105510 A    12/2015
CN        205072356 U    3/2016
(Continued)

OTHER PUBLICATIONS

International Search Report, PCT/CN2017/092409, dated Oct. 11, 2017, dated 3 pages.
(Continued)

*Primary Examiner* — Nabil H Syed
*Assistant Examiner* — Cal J Eustaquio
(74) *Attorney, Agent, or Firm* — Stinson LLP (57) ABSTRACT

A timing reminding method and reminding apparatus for a height-adjustable table. According to the method, by detecting whether a timing starting condition is currently achieved, detecting a posture of a user, and determining a reminding time and starting timing, the user can be reminded to adjust the use posture of the height-adjustable table conveniently and accurately in time. The timing reminding apparatus implements the above timing reminding method.

17 Claims, 6 Drawing Sheets (51) Int. Cl.
 *A61B 5/11* (2006.01)
 *A61B 5/00* (2006.01)
 *A47B 9/00* (2006.01)
 *A47B 13/00* (2006.01)
 *A47B 97/00* (2006.01)

(52) U.S. Cl.
 CPC ............ *A47B 97/00* (2013.01); *A61B 5/1128* (2013.01); *A61B 5/4561* (2013.01); *A61B 5/743* (2013.01); *A61B 5/7405* (2013.01); *A61B 5/748* (2013.01); *A47B 2200/0084* (2013.01)

(56) References Cited

U.S. PATENT DOCUMENTS

| | | | |
|---|---|---|---|
| 10,123,613 | B2 | 11/2018 | Hall et al. |
| 2008/0067738 | A1* | 3/2008 | Shiga ................ B65H 1/04 271/226 |
| 2011/0095044 | A1* | 4/2011 | Sipinski ................ A61L 9/14 222/1 |
| 2014/0015930 | A1* | 1/2014 | Sengupta ................ G06F 21/32 348/46 |

FOREIGN PATENT DOCUMENTS

| | | |
|---|---|---|
| CN | 205547893 U | 9/2016 |
| CN | 105996440 A | 10/2016 |
| CN | 106503615 A | 3/2017 |
| CN | 106510192 A | 3/2017 |
| CN | 106548550 A | 3/2017 |
| DE | 202015003892 U1 | 6/2015 |
| KR | 101651153 B1 | 8/2016 |

OTHER PUBLICATIONS

Written Opinion, PCT/CN2017/092409, dated Oct. 11, 2017, dated 5 pages.

* cited by examiner

TIMING REMINDING METHOD AND REMINDING APPARATUS FOR HEIGHT-ADJUSTABLE TABLE

CROSS-REFERENCE TO RELATED APPLICATIONS

This application is a national stage application of PCT/CN2017/092409, filed Jul. 10, 2017, which claims the benefit of China Patent Application No. 201610932321.4, filed Oct. 24, 2016, the contents of which are incorporated by reference in their entirety for all purposes.

FIELD OF THE INVENTION

The present invention relates to the technical field of furniture, and in particular to a timing reminding method and reminding apparatus for a height-adjustable table.

BACKGROUND OF THE INVENTION

In modern medicine, it was proved that people who bend over tables to work or study for a long time are prone to occupational diseases such as cervical spondylosis, hemorrhoids or the like. If working or learning at a sitting posture or a standing posture alternately, the related occupational diseases can be greatly reduce or relieved. However, the sitting posture and the standing posture have different requirements for the heights of tables, therefore lifting tables of which height is adjustable appear on the market, which can not only satisfy the use demands for working of alternate sitting posture and standing posture, but also can meet the demands of users with different heights.

However, the users are often busy at bending over the tables to work or study and cannot work at alternate sitting posture and standing posture according to a scientific time, and most of them feel that they need to change the office postures after feeling unwell, so that the body health is affected in a long run.

SUMMARY OF THE INVENTION

(1) Technical Problem to be Solved

The object of the present invention is to provide a timing reminding method and reminding apparatus for a height-adjustable table for reminding a user to work at alternate sitting posture and standing posture and for solving the problem that the user easily forgets to adjust the use posture of the height-adjustable table in time.

(2) Technical Solution

In order to solve the above technical problem, the present invention provides a timing reminding method for a height-adjustable table, including:

detecting whether a timing starting condition is currently achieved, wherein the timing starting condition is that a user is in front of the height-adjustable table;

detecting a use posture of the user, and starting timing after determining a reminding time according to the use posture; and when the user maintains the same use posture until a preset reminding time is reached, reminding, by a reminding unit, the user of the height-adjustable table to change the use posture.

Further, during the timing period, if it is detected that the user departs from the height-adjustable table, pausing the current timing, and recording a departure time;

when the departure time of the user away from the height-adjustable table reaches a preset time, resetting the timing after the user returns, and starting the timing after determining the reminding time according to the use posture;

when the departure time of the user away from the height-adjustable table does not reach the preset time, if the user continues to maintain the use posture before leaving after returning, restarting the timing, and continuing the previous timing; and if the user changes the use posture after returning, resetting the timing, and starting the timing after determining the reminding time according to the current use posture; and during the timing period, if the user actively changes the use posture, resetting the timing, and starting the timing after determining the reminding time according to the use posture.

Further, the thermal infrared of the user is detected by a pyroelectric infrared sensor, and a controller judges whether the user is in front of the height-adjustable table according to the detection result; and the use posture of the user is judged by detecting the height of the height-adjustable table by using a first photoelectric sensor, a detection distance of the first photoelectric sensor is set, when the height of the height-adjustable table exceeds the detection distance of the first photoelectric sensor, the first photoelectric sensor cannot received a reflected signal, then the controller judges that the user uses the height-adjustable table at a standing posture, and on the contrary, the controller judges that the user uses the height-adjustable table at a sitting posture.

Further, the height-adjustable table further includes a second photoelectric sensor, the detection distance of the second photoelectric sensor is the same as that of the first photoelectric sensor, the second photoelectric sensor and the first photoelectric sensor are respectively installed at different positions of the height-adjustable table, the installation heights of the two sensors are the same, and when both of the first photoelectric sensor and the second photoelectric sensor cannot receive the reflected signal, the controller judges that the user uses the height-adjustable table at the standing posture; otherwise, the controller judges an abnormal condition and reminds the user to check the state of the height-adjustable table.

Further, the tabletop of the height-adjustable table is further provided with a motion sensor, after the user departs from the height-adjustable table, when the pyroelectric infrared sensor detects that the user is in front of the height-adjustable table again, the controller controls the first photoelectric sensor to start, when the pyroelectric infrared sensor continuously detects that the user is in front of the height-adjustable table, and the motion sensor detects that the tabletop of the height-adjustable table stops moving for a certain period of time, the controller turns off the first photoelectric sensor, and the timing is normally performed; and when the pyroelectric infrared sensor detects that the user is in front of the height-adjustable table, and the motion sensor detects the motion of the tabletop, the controller controls the first photoelectric sensor to start.

Further, the ascending and descending of the tabletop of the height-adjustable table are detected by an acceleration sensor arranged on the height-adjustable table, when the acceleration sensor detects the ascending or descending of the tabletop and when a tabletop static time reaches a preset time after the ascending or descending of the tabletop, the controller judges that the user actively changes the use posture, matches a corresponding reminding time according to the changed use posture and restarts the timing.

Further, whether the user is in front of the height-adjustable table is detected by a sensor combination, and the sensor combination includes a pyroelectric infrared sensor and a first distance measure sensor;

after the pyroelectric infrared sensor detects a thermal infrared signal, the first distance measure sensor starts and detects the distance between the user and the height-adjustable table, and if the distance between the user and the height-adjustable table is greater than a preset distance, the controller judges that the user is not in front of the height-adjustable table; when the distance between the user and the height-adjustable table is less than the preset distance, and the duration reaches a preset time, the controller judges that the user is in front of the height-adjustable table; and wherein, the first distance measure sensor is an acoustic wave distance measure sensor or a third photoelectric sensor.

In another embodiment, whether the user is in front of the height-adjustable table is detected by a sensor combination, the sensor combination includes a pyroelectric infrared sensor and a thermal imaging sensor, after the pyroelectric infrared sensor detects a thermal infrared signal, the thermal imaging sensor starts and continuously detects the thermal infrared signal for a preset time, the controller judges that the user is in front of the height-adjustable table, or otherwise, the controller judges that the user is not in front of the height-adjustable table.

In another embodiment, whether the user is in front of the height-adjustable table is detected by a sensor combination, the sensor combination includes a pyroelectric infrared sensor and an image identification sensor, after the pyroelectric infrared sensor detects a thermal infrared signal, the image identification sensor starts and identifies an image, when the identified image is a preset user, and after the time of continuously identifying that the user is in the image reaches a preset time, the controller judges that the user is in front of the height-adjustable table, or otherwise, the controller judges that the user is not in front of the height-adjustable table.

In another embodiment, a handle switch is arranged on the height-adjustable table, and when the user triggers the handle switch, it is judged that the user is in front of the height-adjustable table.

In another embodiment, the height of the tabletop of the height-adjustable table is judged by using a proximity switch or a magnetic induction switch arranged on the height-adjustable table, when the tabletop of the height-adjustable table descends below a preset height, the proximity switch or the magnetic induction switch is triggered, and then the controller judges that the user is at the sitting posture; and when the proximity switch or the magnetic induction switch is not triggered, the controller judges that the user is at the standing posture.

In another embodiment, the ascending and descending of the tabletop of the height-adjustable table are detected by an acceleration sensor arranged on the height-adjustable table, when the acceleration sensor detects the ascending or descending of the tabletop and when a tabletop static time reaches a preset time after the ascending or descending of the tabletop, the controller judges that the user actively changes the use posture, matches a corresponding reminding time according to the changed use posture and restarts the timing.

In another embodiment, the height of the tabletop of the height-adjustable table is measured by using a second distance measure sensor arranged on the height-adjustable table, when the height is greater than a preset value, the controller judges that the user is at a standing posture, or otherwise, the controller judges that the user is at a sitting posture.

The present invention further provides a timing reminding apparatus for a height-adjustable table, including:

a first photoelectric sensor used for detecting the height of the height-adjustable table;

a pyroelectric infrared sensor used for detecting whether a user is in front of the height-adjustable table;

a reminding unit used for sending reminding; and a controller used for receiving detection information of the first photoelectric sensor and the pyroelectric infrared sensor, and sending a control command to the first photoelectric sensor, the pyroelectric infrared sensor and the reminding unit.

Further, the first photoelectric sensor, the pyroelectric infrared sensor, the reminding unit and the controller are all arranged in a shell, the first photoelectric sensor is arranged below the shell, the pyroelectric infrared sensor is arranged on a front side of the shell, and the shell is provided with a bayonet matching the tabletop.

Further, the timing reminding apparatus further includes a motion sensor, and the motion sensor is connected with the controller for detecting a motion state of the tabletop of the height-adjustable table.

Further, at least one second photoelectric sensor is further provided, the second photoelectric sensor is connected with the controller, and the second photoelectric sensor and the first photoelectric sensor are respectively arranged on two opposite sides of the height-adjustable table, and the two sensors have the same installation height.

Further, the timing reminding apparatus further includes a touch display screen used for inputting related setting information and used for displaying text reminding.

Further, the reminding unit includes a sound reminding module and/or an LED prompting lamp, and both of the sound reminding module and/or the LED prompting lamp are connected with the controller for sending sound reminding and/or LED prompting lamp flashing reminding.

The present invention further provides another timing reminding apparatus for a height-adjustable table, including:

a sensor combination used for detecting whether a user is in front of the height-adjustable table;

the sensor combination includes a pyroelectric infrared sensor and a first distance measure sensor; or the sensor combination includes a pyroelectric infrared sensor and a thermal imaging sensor; or the sensor combination includes a pyroelectric infrared sensor and an image identification sensor; and a proximity switch, a magnetic induction switch or a second distance measure sensor arranged on the height-adjustable table for judging a use posture of the user; and a controller used for receiving detection information of the sensor combination and the proximity switch or the magnetic induction switch, matching a reminding time according to the received information and timing.

Further, the timing reminding apparatus further includes a touch display screen used for inputting related setting information and used for displaying text reminding.

Further, the timing reminding apparatus further includes a reminding unit, the reminding unit includes a sound reminding module and/or an LED prompting lamp, and both of the sound reminding module and/or the LED prompting lamp are connected with the controller for sending sound reminding and/or LED prompting lamp flashing reminding.

Further, the timing reminding apparatus further includes a Bluetooth module or a wireless module for connecting with a mobile terminal or a cloud.

(3) Beneficial Effects

The above technical solution of the present invention has the following advantages: in the timing reminding method applied to the height-adjustable table provided by the present invention, timing is performed according to the detected use state and use posture of the user, and the corresponding reminding time is determined, so that the user can be reminded to adjust the use posture of the height-adjustable table conveniently and accurately in time.

In the figures: 1: height-adjustable table; 11: tabletop; 2: timing reminding apparatus; 21: controller; 22: pyroelectric infrared sensor; 23: first photoelectric sensor; 24: LED prompting lamp; 25: sound reminding module; 26: motion sensor; 27: shell; 271: bayonet; 28: touch display screen; 29: second photoelectric sensor.

DETAILED DESCRIPTION OF THE EMBODIMENTS

In order that the purposes, technical solutions and advantages of the present invention are clearer, a clear and complete description of the technical solutions in the embodiments of the present invention will be given below, in combination with the drawings in the embodiments of the present invention. Apparently, the embodiments described below are merely a part, but not all, of the embodiments of the present invention. All of other embodiments, obtained by those of ordinary skill in the art based on the embodiments of the present invention without any creative effort, fall into the protection scope of the present invention.

In the description of the present invention, the terms "first", "second" and "third" are used for descriptive purposes only, and cannot be construed as indicating or implying the relative importance.

In the description of the present invention, it should be noted that, unless otherwise expressly stated and limited, the terms "installation", "connected" and "connection" should be understood broadly, for example, can be a fixedly connected, detachably connected or integrally connected; can be a mechanical connection or an electrical connection; cam be directly connected or indirectly connected through an intermediate medium, and can be internal communication between two elements. For those of ordinary skill in the art, the specific meanings of the above terms in the present invention can be understood according to specific circumstances.

First Embodiment

Figure 1:
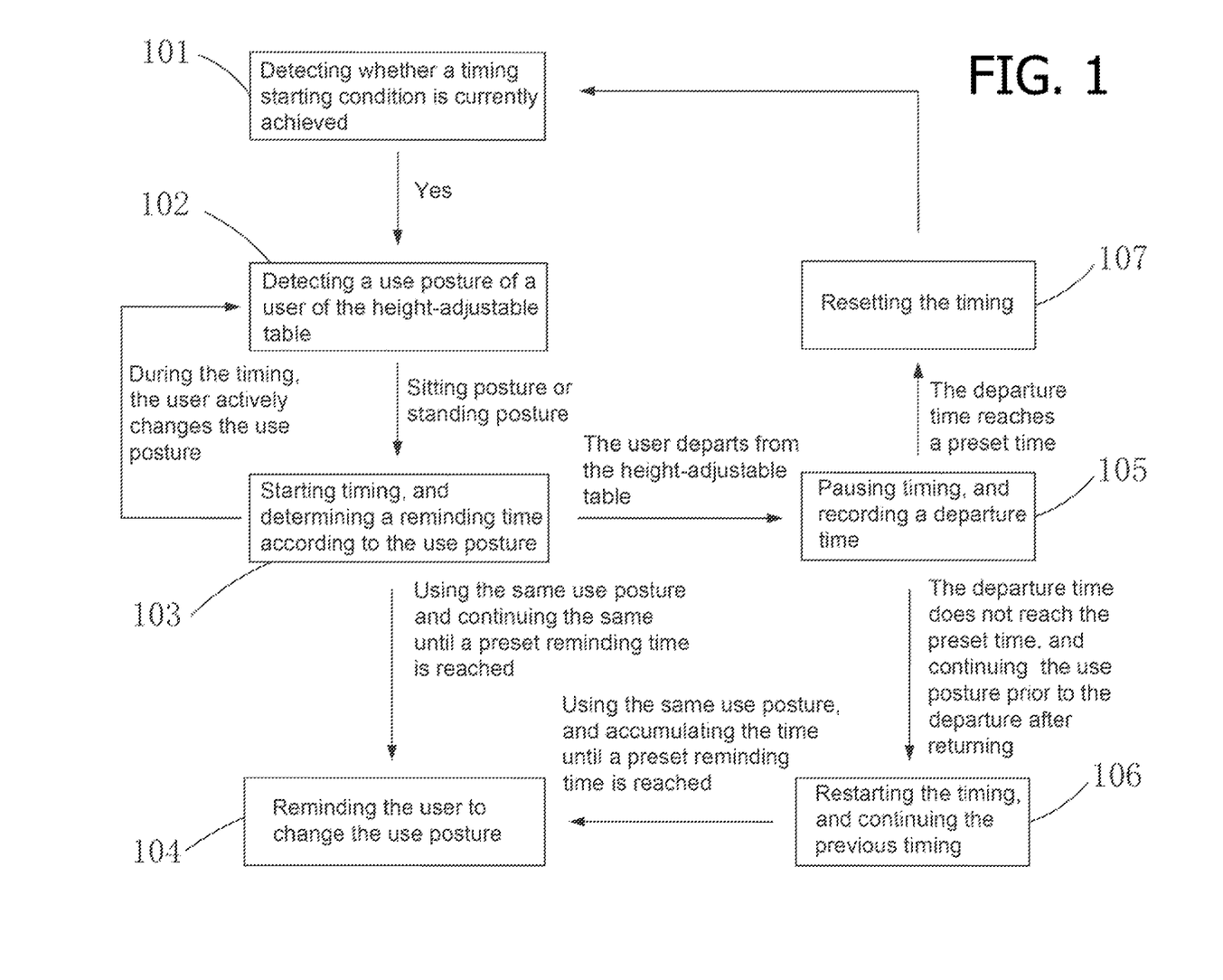
FIG. 1 is a flowchart of a timing reminding method for a height-adjustable table in a first embodiment of the present invention.

As shown in FIG. 1, a timing reminding method for a height-adjustable table provided by an embodiment of the present invention includes the following steps:

Step 101: detecting whether a timing starting condition is currently achieved, wherein the timing starting condition is that a user is in front of the height-adjustable table. If the detection result is that there is no user in front of the height-adjustable table, the timing is not started.

Further, in the step 101, the thermal infrared released by the user is detected by a pyroelectric infrared sensor, whether the user is in front of the height-adjustable table is determined accordingly, and the detection result is sent to a controller. If it is detected that the user is in front of the height-adjustable table, then a step 102 is continued.

It should be noted that, detecting whether the user is in front of the height-adjustable table by using the pyroelectric infrared sensor is a preferred solution of the present embodiment, and a thermal imaging sensor or an image sensor can also achieve the purpose of detecting whether the user is in front of the height-adjustable table.

Step 102: detecting a use posture of the user, and starting timing after determining a reminding time according to the use posture, wherein the use posture includes a sitting posture and a standing posture. Specifically, whether the use posture of the user is the sitting posture or the standing posture is judged by detecting the height of the height-adjustable table by using a first photoelectric sensor, a detection distance of the first photoelectric sensor is set, and the detection distance is related to the use height of the height-adjustable table when the user is at the sitting posture and an installation position of the first photoelectric sensor.

In the present embodiment, a desktop type height-adjustable table is taken as an example, and it is placed on a table or other supporting platforms for use, therefore the distance between the height-adjustable table and the tabletop is smaller, it is set that when the height of the height-adjustable table is less than 180 mm, the user uses the height-adjustable table at the sitting posture, and when the height of the height-adjustable table exceeds 180 mm, the user uses the height-adjustable table at the standing posture, the first photoelectric sensor is installed on the lower side of the tabletop of the height-adjustable table, the detection distance is set according to the specific installation position, for example, if the first photoelectric sensor protrudes 20 mm from the lower side of the tabletop, the detection distance of the first photoelectric sensor is set as 160 mm, when the height of the height-adjustable table exceeds 180 mm, the first photoelectric sensor cannot receive a reflected signal, then the controller judges that the user uses the height-adjustable table at the standing posture, and on the contrary, the controller judges that the user uses the height-adjustable table at the sitting posture.

Preferably, the first photoelectric sensor is a diffused reflection type photoelectric sensor, a light emitter and a light receiver are installed in its sensing head, and the light emitted by the light emitter cannot be found when the detection distance goes beyond. When a detection object is within the detection distance and reflects a part of light, the light receiver receives a light signal.

After the use posture of the user is judged, a step 103 is continued, and the step includes: determining the reminding time according to the posture of the user, and starting timing. For example, when it is judged that the posture of the user is a sitting posture, a preset sitting posture reminding time is 60 minutes, the timing is started, after the sitting posture is maintained for 60 minutes, a step 104 is executed, a reminding unit reminds the user to raise the height of the height-adjustable table to adapt to the change from the sitting posture to the standing posture. At this time, the timing is reset, and the present reminding time is determined according to a preset standing posture reminding time, the preset standing posture reminding time is 20 minutes, and after the standing posture is maintained for 20 minutes, the reminding unit reminds the user to lower the height of the height-adjustable table again to adapt to the change from the standing posture to the sitting posture.

If it is detected that the user departs from the height-adjustable table during the timing period, a step 105 is executed, that is, the current timing is paused, a departure time is recorded, when the departure time exceeds a preset time, a step 107 is executed, that is, the timing is reset to be zero, and then the step 101 is executed; when the departure time does not exceed the preset time, and the user continues to maintain use posture prior to the departure after returning, a step 106 is executed, that is, the timing is restarted, the previous timing is continued, when the accumulated time the use posture is maintained reaches the preset reminding time, the step 104 is executed, that is, the reminding unit reminds the user of the height-adjustable table to change the use posture.

Preferably, the preset time of departing from the height-adjustable table is 2 minutes.

If the user actively changes the use posture during the timing period, the timing is reset, and the step 102 is executed.

Specifically, the ascending and descending of the tabletop of the height-adjustable table can be detected by an acceleration sensor arranged on the height-adjustable table, when the acceleration sensor detects the ascending or descending of the tabletop and when a tabletop static time reaches a preset time after the ascending or descending of the tabletop, the controller judges that the user actively changes the use posture, matches a corresponding reminding time according to the changed use posture and restarts the timing.

It can be seen from the step 101 to the step 104 that the present invention performs the timing and determines the corresponding reminding time according to the detected use state and the use posture of the user, and can remind the user to adjust the use posture of the height-adjustable table in time.

It can be seen from the step 105 to the step 107 that the present invention solves various situations that may occur during the use of the user, and can accurately remind the user to adjust the use posture of the height-adjustable table under different use conditions in time.

It should be noted that, in the present embodiment, the height of the height-adjustable table is the distance between the tabletop of the height-adjustable table and its supporting surface (the tabletop or other supporting platform surfaces for supporting the height-adjustable table).

Figure 2:
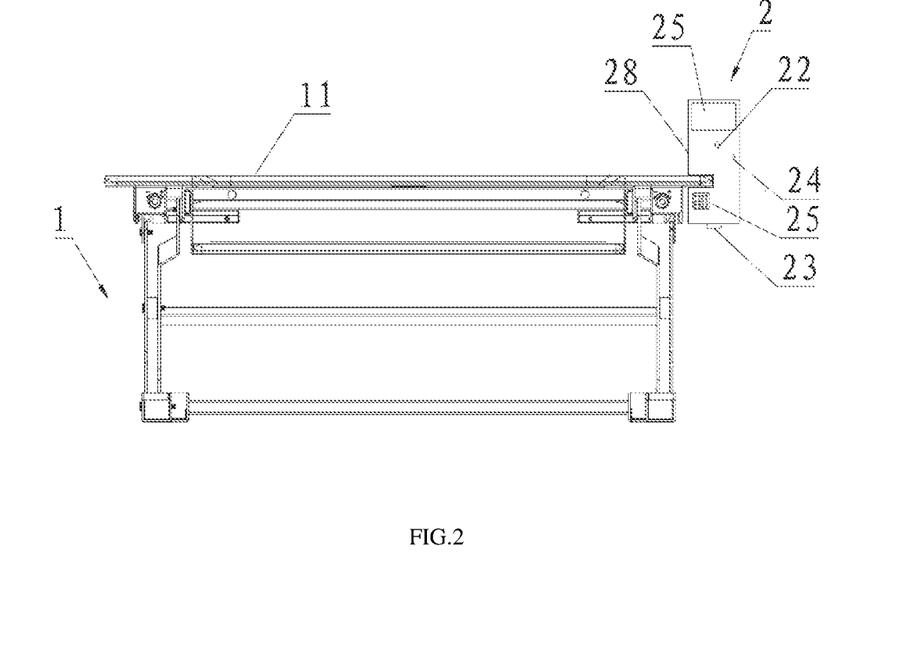
FIG. 2 is a schematic diagram after a timing reminding apparatus is installed on the height-adjustable table in the first embodiment of the present invention.
Figure 3:
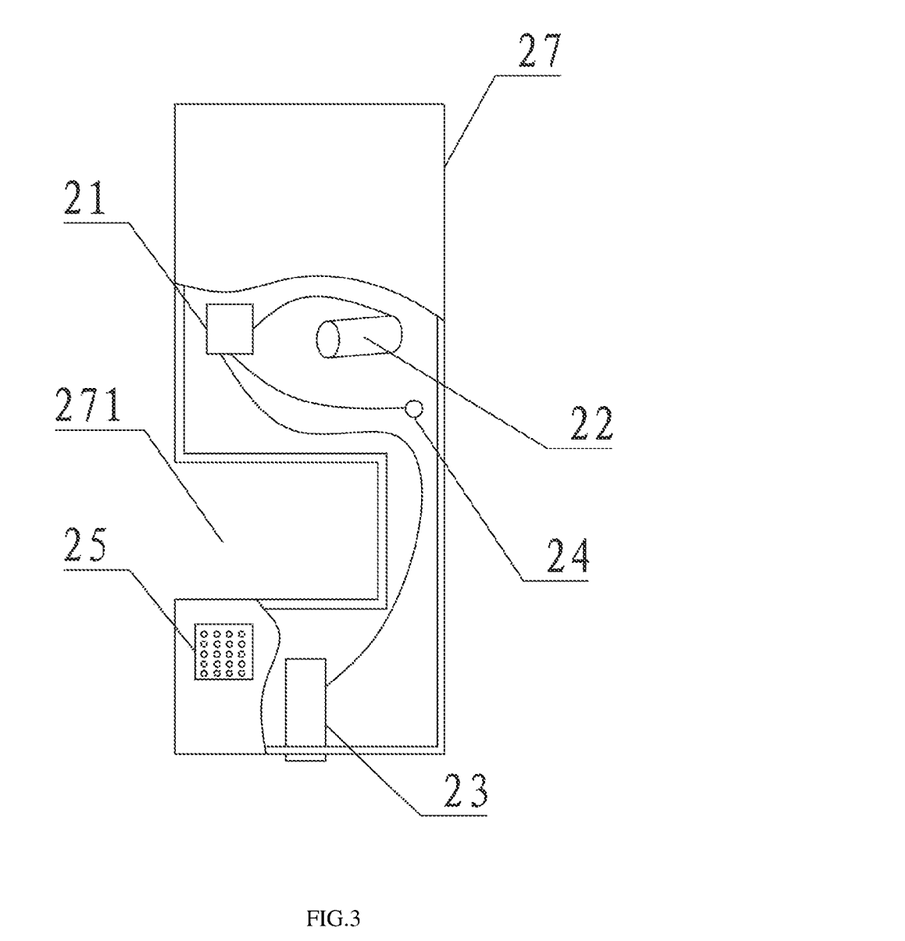
FIG. 3 is a schematic diagram of an internal structure of the timing reminding apparatus in the first embodiment of the present invention.

The present embodiment further provides a timing reminding apparatus for a height-adjustable table. As shown in FIG. 2 and FIG. 3, the timing reminding apparatus 2 includes a controller 21, a pyroelectric infrared sensor 22, a first photoelectric sensor 23 and a reminding unit, wherein both of the pyroelectric infrared sensor 22 and the first photoelectric sensor 23 are respectively connected with the controller 21 for sending detection information to the controller for processing. Specifically, the first photoelectric sensor 23 is used for detecting the height of the height-adjustable table 1, and the pyroelectric infrared sensor 22 is used for detecting whether the user is in front of the height-adjustable table 2; and the reminding unit is connected with the controller 21 for sending reminding after receiving an enable signal of the controller 21.

Specifically, the reminding unit includes a sound reminding module 25 and/or an LED prompting lamp 24, at the arrival of the reminding time, the sound reminding module 25 generates sound or vibration reminding, and the LED prompting lamp emits flashing reminding.

Figure 4:
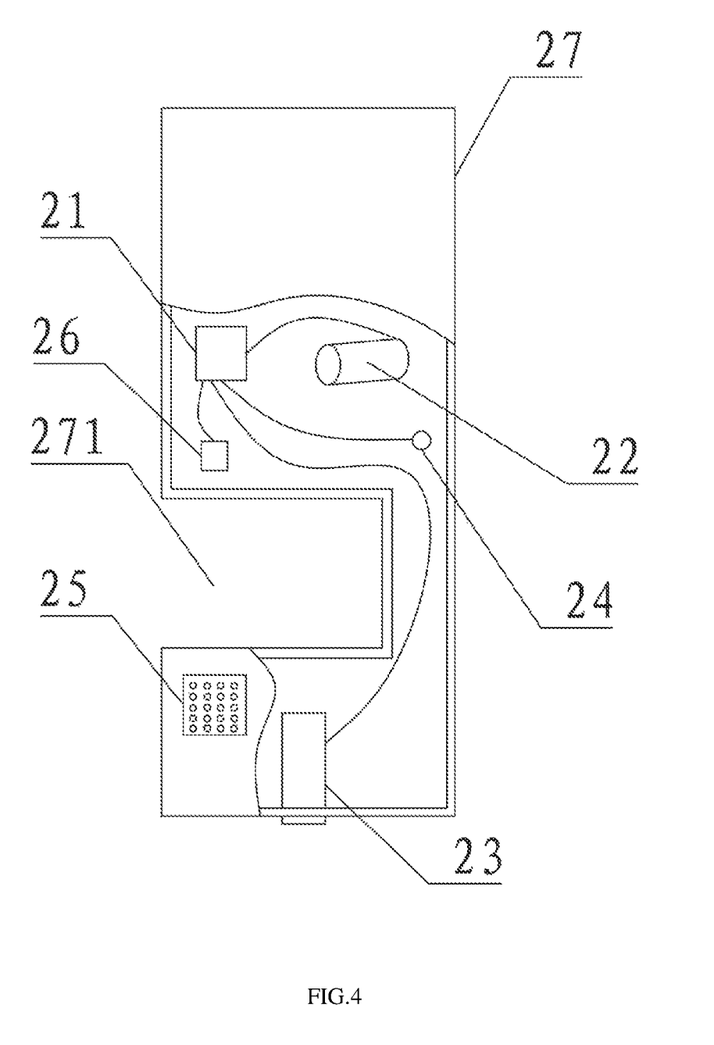
FIG. 4 is a schematic diagram of an internal structure of a timing reminding apparatus in a second embodiment of the present invention.

Further, the first photoelectric sensor 23, the pyroelectric infrared sensor 22, the reminding unit and the controller 21 are all arranged in a shell 27 to form a module, thereby being convenient to use and install and to protect the first photoelectric sensor 23, the pyroelectric infrared sensor 22, the reminding unit and the controller 21 to a certain extent. As shown in FIG. 4, the shell 27 is provided with a bayonet 271 matching the tabletop 11 and is directly clamped and fixed on one side of the tabletop 11 in use, thereby being convenient to install without presetting an installation structure on the tabletop 11.

Further, in order to improve the versatility of the timing reminding apparatus 2, an elastic clamping means (not shown in the figure) is arranged in the bayonet 271. Specifically, a spring is installed on at least one side of the bayonet 271, a fixing plate is arranged on the lower side of the spring, during clamping, the fixing plate presses the spring and is contact with the tabletop 11, so that the timing reminding apparatus 2 can be conveniently installed on the desktops 11 with different thicknesses.

Preferably, springs and corresponding fixing plates are installed on both sides of the bayonet 271, during the installation, the two fixing plates are in contact with the tabletop, and the desktops 11 with different thicknesses can be adapted to by a compression spring.

Specifically, the first photoelectric sensor 23 is arranged below the shell 27, and a sensing head of which penetrates through the shell 27 and is vertically downward. The pyroelectric infrared sensor 22 is arranged on a front side of the shell 27, and the sensing head of which penetrates through the shell 27 and deviates toward the middle of the front side (the side where the user is located during the use) of the height-adjustable table 1, so that the detection range of the pyroelectric infrared sensor 22 can cover the front side of the entire desktop 11.

Second Embodiment

As shown in FIG. 4, the timing reminding apparatus of the second embodiment is basically the same as that of the first embodiment, the same points are not described repeatedly again, and the difference lies in that: a motion sensor 26 is further provided, the motion sensor 26 is connected with the controller 21 for detecting a motion state of the height-adjustable table, and sending a detected signal to the controller, the controller sends an enable signal to the first photoelectric sensor after receiving a desktop motion signal of the height-adjustable table, and the first photoelectric sensor 23 starts working, so that unnecessary waste caused by unnecessary continuous work is avoided without affecting the normal work of the timing reminding apparatus 2.

Specifically, the motion sensor is a triaxial acceleration sensor (triaxial accelerometer), a gyroscope, or a geomagnetic sensor.

The method for performing timing reminding by using the timing reminding apparatus 2 of the present embodiment is as follows: after the user departs from the height-adjustable table 1, when the pyroelectric infrared sensor 22 detects that the user is in front of the height-adjustable table 1 again, the controller 21 controls the first photoelectric sensor 23 to start, when the pyroelectric infrared sensor 22 continuously detects that the user is in front of the height-adjustable table 1, and the motion sensor 26 detects that the tabletop 11 of the height-adjustable table 1 stops moving for a certain period of time, the controller 21 turns off the first photoelectric sensor 23, the timing is normally performed, and the reminding unit sends reminding at the arrival of the reminding time.

When the pyroelectric infrared sensor 22 detects that the user is in front of the lift table 1, and the motion sensor 26 detects that the tabletop 11 moves, the controller 21 controls the first photoelectric sensor 23 to start.

Preferably, the controller 21 turns off the first photoelectric sensor 23 after the tabletop 11 stops moving for 2 minutes.

Third Embodiment

Figure 5:
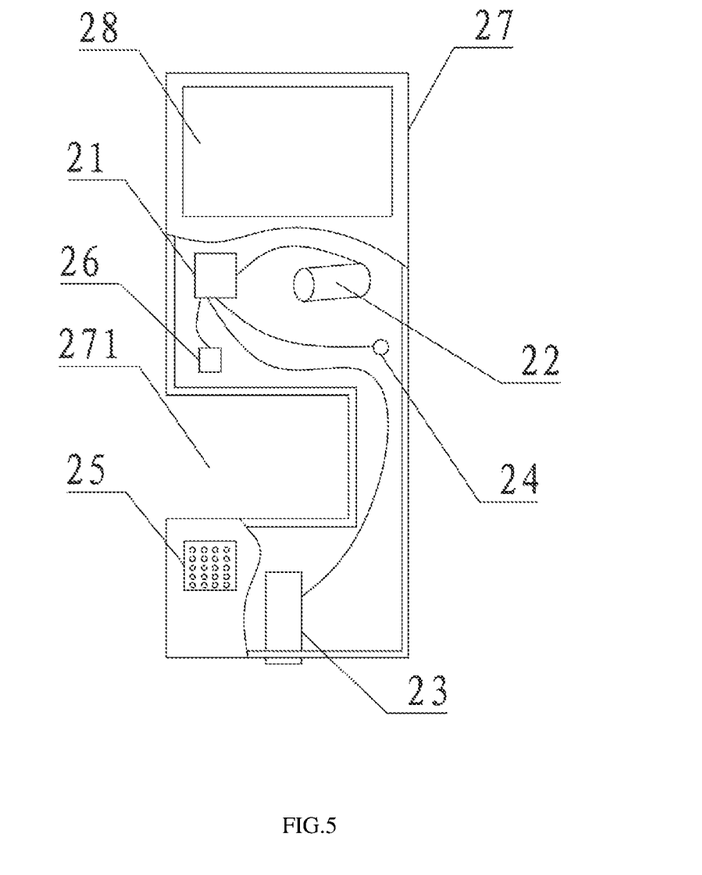
FIG. 5 is a schematic diagram of an internal structure of a timing reminding apparatus in a third embodiment of the present invention.

As shown in FIG. 5, the timing reminding apparatus of the third embodiment is basically the same as that of the first embodiment or the second embodiment, the same points are not described repeatedly again, and the difference lies in that: the timing reminding apparatus 2 further includes a touch display screen 28, and the touch display screen 28 is arranged on the front side of the shell 27 and is used for performing human-computer interaction, inputting a preset time or displaying text reminding and other information.

Fourth Embodiment

Figure 6:
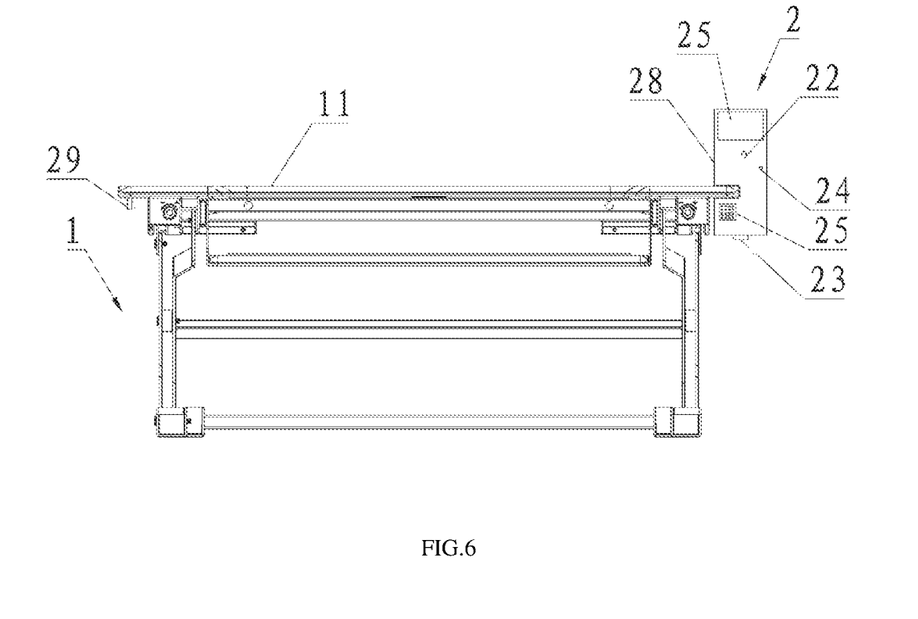
FIG. 6 is a schematic diagram after a timing reminding apparatus is installed on a height-adjustable table in a fourth embodiment of the present invention.

As shown in FIG. 6, the timing reminding apparatus of the fourth embodiment is basically the same as that of the first embodiment or the second embodiment or the third embodiment, the same points are not described repeatedly again, and the difference lies in that: the timing reminding apparatus 2 further includes a second photoelectric sensor 29, both of the second photoelectric sensor 29 and the first photoelectric sensor 23 are connected with the controller 21 and are respectively installed on two opposite sides of the tabletop 11, the two sensors have the same installation height and play a mutual verification role in use, when the two sensors have the same detection result, that is, both of the two sensors can receive reflection information or neither of the two sensors can receive the reflection information, the controller judges that the user is at the standing posture or the sitting posture at present, otherwise, the controller judges an abnormal situation and performs reminding through the reminding unit, thereby avoiding the inaccuracy of the result caused by sundries on the lower side of the desktop 11 or tilting of the desktop 11.

It should be noted that the present invention includes, but not limited to, two photoelectric sensors. In the present embodiment, it is a preferred embodiment of the present invention that one photoelectric sensor is respectively arranged on the two opposite sides of the table. According to the principle, one or more photoelectric sensors can be respectively arranged on three or four side faces of the table to eliminate the interference signal as much as possible, so that the detection result is more accurate.

Fifth Embodiment

In the present embodiment, whether the user is in front of the height-adjustable table is detected by a sensor combination, the sensor combination is the combination of a pyroelectric infrared sensor (PIR) and a first distance measure sensor in the present embodiment, wherein after the pyroelectric infrared sensor continuously detects a thermal infrared signal for a preset time, the first distance measure sensor starts and senses the distance between the user and the height-adjustable table, and if the distance between the user and the height-adjustable table is greater than a preset distance, the controller judges that the user is not using the height-adjustable table, and then, the timing is not started.

The first distance measure sensor is an acoustic wave distance measure sensor or a third photoelectric sensor or the like.

If the first distance measure sensor detects that the distance between the user and the height-adjustable table is less than the preset distance and the time for maintaining the distance being less than the preset distance reaches a preset time, the controller judges that the user is using the height-adjustable table, then the controller matches a corresponding reminding time according to the use posture and starts the timing.

In the present embodiment, the first distance measure sensor detects that the distance between the user and the height-adjustable table is less than the preset distance and the time for maintaining the distance being less than the preset distance reaches the preset time in the following manner: the first distance measure sensor continuously detects that the distance of the user is less than 80 cm within 2 minutes, of course, the distance is related to the installation position of the distance measure sensor, as long as within a normal distance range in which the user can use the height-adjustable table, and this distance can be autonomously set according to the experience and the situation of the user.

It should be noted that, the continuous detection in the present embodiment can be continuous detection and can also be continuous interval detection with a specified interval time within a certain period of time.

The use posture of the user can be judged by any of the judgment modes of the user posture in the first, second or fourth embodiment.

The height of the tabletop of the height-adjustable table can also be judged by using a proximity switch or a magnetic induction switch arranged on the height-adjustable table. Specifically, a sensing portion and a sensed portion of the proximity switch or the magnetic induction switch are arranged at different positions of the tabletop of the height-adjustable table according to a certain spacing distance, when the lifting height of the height-adjustable table is adjusted, the spacing distance between the sensing portion and the sensed portion changes, when the tabletop of the height-adjustable table descends below a preset height, the proximity switch or the magnetic induction switch is triggered, that is, the sensing portion senses the sensed portion and sends a signal to the controller, and then the controller judges that the user is at the sitting posture; and when the proximity switch or the magnetic induction switch is not triggered, the controller judges that the user is at the standing posture.

The height of the tabletop of the height-adjustable table can also be measured by using a second distance measure sensor arranged on the lower side of the height-adjustable table, when the height is greater than a preset value, the controller judges that the user is at the standing posture, and when the height is less than the preset value, the controller judges that the user is at the sitting posture. The preset value is preferably 15 cm, that is, when the height exceeds 15 cm, the controller judges that the user is at the standing posture, and when the height is less than 15 cm, the controller judges that the user is at the sitting posture. The distance setting can be autonomously set according to the height and habits of the user.

The second distance measure sensor is a second acoustic wave sensor or a fourth photoelectric sensor. The height measured by the second distance measure sensor can be played by sound, and can also be displayed by a means such as a display screen.

It should be noted that, the maximum lifting height of the height-adjustable table (the height of the tabletop from the worktable on the lower side) may be 60 cm.

Sixth Embodiment

The sixth embodiment can use any of the use posture judgment manners in the above embodiments, and thus would not be repeatedly described, the difference between the present sixth embodiment and the above embodiments lies in the difference of the used sensor combination. Specifically, the sensor combination in the present embodiment includes a pyroelectric infrared sensor and a thermal imaging sensor, after the pyroelectric infrared sensor detects a thermal infrared signal, the controller controls the thermal imaging sensor to start, after the thermal imaging sensor continuously detects the thermal infrared signal for a preset time, the controller judges that the user is in front of the height-adjustable table, or otherwise, the controller judges that the user is not in front of the height-adjustable table. In the present embodiment, the continuous detection of the thermal infrared signal time reaching the preset time means that the thermal infrared signal is continuously detected for 4-8 times within 2 minutes, and if the thermal infrared signal can be detected in the last detection and the total times of detecting the infrared signal reach more than 90% of the total detection times, it is absolutely judged that the user is in front of the height-adjustable table; if the times of detecting the infrared signal are less than 10% of the total detection times, it is absolutely judged that the user is not in front of the height-adjustable table; and if the times of not detecting the thermal infrared signal or detecting the thermal infrared signal in the last detection are less than the total detection times and are 10-90% of the total detection times (excluding 10% and 90%), a detection time of 1 minute is added, whether the user is in front of the height-adjustable table is judged according to a percentage of the times of detecting the thermal infrared signal within the detection time, and in the present embodiment, the judgment criterion also uses 10% and 90% as critical points.

Since the pyroelectric infrared sensor can only better detect the thermal infrared signal of a moving object, the combination with the thermal imaging sensor not only solves the problem and achieves the thermal infrared signal of a stationary object, and after the pyroelectric infrared sensor detects the thermal infrared signal, the thermal imaging sensor is started to better save the energy.

It should be noted that, the detection time and the detection interval can be freely set as needed.

Seventh Embodiment

The seventh embodiment can use any of the use posture judgment manners in the above embodiments, and thus would not be repeatedly described, the difference between the present seventh embodiment and the above embodiments lies in the difference of the used sensor combination. Specifically, the sensor combination in the present embodiment includes a pyroelectric infrared sensor and an image identification sensor, after the pyroelectric infrared sensor detects a thermal infrared signal, the image identification sensor starts and identifies an image, if the user is continuously identified in the image for a preset time, it is judged that the user is using the height-adjustable table, or otherwise, it is judged that the user is not using the height-adjustable table.

It should be noted that the present embodiment performs the identification according to the information pre-input into the image identification sensor. A humanoid profile can be input, and a specific user can also be input. It can be universal, it is only identified that the user is in the front, or only the specific user is identified, or different users are identified, and then personalized preset times of the corresponding users are matched.

Eighth Embodiment

In the present embodiment, whether the user is in front of the height-adjustable table is detected by a handle switch arranged on the height-adjustable table, when the user triggers the handle switch, the controller judges that the user is in front of the height-adjustable table, matches a corresponding reminding time according to the current use posture of the user, and starts timing.

The use posture of the user can be judged by any one of the judgment modes of the use posture in the above embodiments.

Ninth Embodiment

The ninth embodiment provides a timing reminding apparatus for a height-adjustable table, including a controller, a sensor combination, a proximity switch and a magnetic induction switch arranged on the height-adjustable table, and specifically, the sensor combination includes a pyroelectric infrared sensor and a distance measure sensor; or includes the pyroelectric infrared sensor and a thermal imaging sensor; or includes the pyroelectric infrared sensor and an image identification sensor; and further, the proximity switch or the magnetic induction switch is further arranged on the height-adjustable table, specifically, a sensing portion and a sensed portion of the proximity switch or the magnetic induction switch are arranged at different positions on the tabletop of the height-adjustable table at a certain spacing distance, when the lifting height of the height-adjustable table is adjusted, the spacing distance between the sensing portion and the sensed portion changes, when the tabletop of the height-adjustable table descends below a preset height, the proximity switch or the magnetic induction switch is triggered, that is, the sensing portion senses the sensed portion and sends a signal to the controller, and then the controller judges that the user is at a sitting posture; and when the proximity switch or the magnetic induction switch is not triggered, the controller judges that the user is at a standing posture.

Further, the timing reminding apparatus in the present embodiment further includes a reminding unit, the reminding unit includes a sound reminding module and/or an LED prompting lamp, and both of the sound reminding module and/or the LED prompting lamp are connected with the controller for generating sounding reminding and/or LED prompting lamp flashing reminding.

Further, the timing reminding apparatus further includes a touch display screen used for inputting related setting information and used for displaying text reminding.

Preferably, the timing reminding apparatus further includes a Bluetooth module or a wireless module used for connecting with a mobile terminal or a cloud and capable of transmitting information input or used by the user to the mobile terminal or the cloud, and whether the user is in front of the height-adjustable table can also be judged or assistantly judged through the connection situation of the Bluetooth module or the wireless module and the user.

In summary, in the timing reminding method applied to the height-adjustable table provided by the present invention, timing is performed according to the detected use state and the use posture of the user, and the corresponding reminding time is determined, so that the user can be conveniently and accurately reminded to adjust the user posture of the height-adjustable table in time.

Finally, it should be noted that the above embodiments are merely used for illustrating the technical solutions of the present invention, rather then limiting the same; although the present invention has been described in detail with reference to the foregoing embodiments, those of ordinary skill in the art should understand that, they can still make modifications to the technical solutions recorded in the foregoing embodiments, or make equivalent substitutions to a part of technical features; and these modifications or substitutions do not make the essence of the corresponding technical solutions deviate from the spirit and scope of the technical solutions of the various embodiments of the present invention.

The invention claimed is:

1. A timing reminding method for a height-adjustable table, comprising:
   detecting whether a timing starting condition is currently achieved, wherein the timing starting condition is that a user is in front of the height-adjustable table;
   wherein whether the user is in front of the height-adjustable table is detected by a pyroelectric infrared sensor and another sensor selected from a first distance measure sensor, a thermal imaging sensor, or an image identification sensor;
   after the pyroelectric infrared sensor detects a thermal infrared signal, then
      the first distance measure sensor starts and detects the distance between the user and the height-adjustable table, and if the distance between the user and the height-adjustable table is greater than a preset distance, a controller judges that the user is not in front of the height-adjustable table; and when the distance between the user and the height-adjustable table is less than the preset distance, and the duration reaches a preset time, the controller judges that the user is in front of the height-adjustable table, wherein the another sensor is the first distance measure sensor;
      the thermal imaging sensor starts and continuously detects the thermal infrared signal for a preset time, the controller judges that the user is in front of the height-adjustable table, or otherwise, the controller judges that the user is not in front of the height-adjustable table, wherein the another sensor is the thermal imaging sensor; or
      the image identification sensor starts and identifies an image, when the identified image is a preset user, and after the time of continuously identifying that the user is in the image reaches a preset time, the controller judges that the user is in front of the height-adjustable table, or the controller judges that the user is not in front of the height-adjustable table, wherein the another sensor is the image identification sensor;
   detecting a use posture of the user, determining a corresponding reminding time according to the use posture, and starting timing; and
   when the user maintains the same use posture until a preset reminding time is reached, reminding, by a reminding unit, the user of the height-adjustable table to change the use posture.

2. The method according to claim 1, wherein: during the timing period, if it is detected that the user departs from the height-adjustable table, pausing the current timing, and recording a departure time;
   when the departure time of the user away from the height-adjustable table reaches a preset time, resetting the timing after the user returns, and starting the timing after determining the reminding time according to the use posture;
   when the departure time of the user away from the height-adjustable table does not reach the preset time, if the user continues to maintain the use posture before leaving after returning, restarting the timing, and continuing the previous timing; and if the user changes the use posture after returning, resetting the timing, and starting the timing after determining the reminding time according to the current use posture; and
   during the timing period, if the user actively changes the use posture, resetting the timing, and starting the timing after determining the reminding time according to the use posture.

3. The method according to claim 1, wherein: the thermal infrared signal of the user is detected by the pyroelectric infrared sensor, and the controller judges whether the user is in front of the height-adjustable table according to the detection result; and
   the use posture of the user is judged by detecting the height of the height-adjustable table by using a first photoelectric sensor, a detection distance of the first photoelectric sensor is set, when the height of the height-adjustable table exceeds the detection distance of the first photoelectric sensor, the first photoelectric sensor cannot receive a reflected signal, then the controller judges that the user uses the height-adjustable table at a standing posture, and on the contrary, the controller judges that the user uses the height-adjustable table at a sitting posture.

4. The method according to claim 3, further comprising: a second photoelectric sensor, wherein the detection distance of the second photoelectric sensor is the same as that of the first photoelectric sensor, the second photoelectric sensor and the first photoelectric sensor are respectively installed at different positions of the height-adjustable table, the installation heights of the two sensors are the same, and when both of the first photoelectric sensor and the second photoelectric sensor cannot receive the reflected signal, the controller judges that the user uses the height-adjustable table at the standing posture; otherwise, the controller judges an abnormal condition and reminds the user to check the state of the height-adjustable table.

5. The method according to claim 3, wherein: the tabletop of the height-adjustable table is further provided with a motion sensor, after the user departs from the height-adjustable table, when the pyroelectric infrared sensor detects that the user is in front of the height-adjustable table again, the controller controls the first photoelectric sensor to start, when the pyroelectric infrared sensor continuously detects that the user is in front of the height-adjustable table, and the motion sensor detects that the tabletop of the height-adjustable table stops moving for a certain period of time, the controller turns off the first photoelectric sensor, and the timing is normally performed; and when the pyroelectric infrared sensor detects that the user is in front of the height-adjustable table, and the motion sensor detects the motion of the tabletop, the controller controls the first photoelectric sensor to start.

6. The method according to claim 1, wherein: a handle switch is arranged on the height-adjustable table, and when the user triggers the handle switch, it is judged that the user is in front of the height-adjustable table.

7. The method according to claim 1, wherein: the height of the tabletop of the height-adjustable table is judged by using a proximity switch or a magnetic induction switch arranged on the height-adjustable table, when the tabletop of the height-adjustable table descends below a preset height, the proximity switch or the magnetic induction switch is triggered, and then the controller judges that the user is at a sitting posture; and when the proximity switch or the magnetic induction switch is not triggered, the controller judges that the user is at a standing posture.

8. The method according to claim 2, wherein: the ascending and descending of the tabletop of the height-adjustable table are detected by an acceleration sensor arranged on the height-adjustable table, when the acceleration sensor detects the ascending or descending of the tabletop and when a tabletop static time reaches a preset time after the ascending or descending of the tabletop, the controller judges that the user actively changes the use posture, matches a corresponding reminding time according to the changed use posture and restarts the timing.

9. The method according to claim 1, wherein: the height of the tabletop of the height-adjustable table is measured by using a second distance measure sensor arranged on the height-adjustable table, when the height is greater than a preset value, the controller judges that the user is at a standing posture, or otherwise, the controller judges that the user is at a sitting posture.

10. A timing reminding apparatus for a height-adjustable table, comprising:
   a first photoelectric sensor used for detecting the height of the height-adjustable table;
   a pyroelectric infrared sensor used for detecting whether a user is in front of the height-adjustable table;
   a reminding unit used for sending reminding; and
   a controller used for receiving detection information of the first photoelectric sensor and the pyroelectric infrared sensor, sending a control command to the first photoelectric sensor, the pyroelectric infrared sensor and the reminding unit, matching a reminding time according to the received information, and timing.

11. The timing reminding apparatus according to claim 10, wherein: the first photoelectric sensor, the pyroelectric infrared sensor, the reminding unit and the controller are all arranged in a shell, the first photoelectric sensor is arranged below the shell, the pyroelectric infrared sensor is arranged on a front side of the shell, and the shell is provided with a bayonet matching the tabletop.

12. The timing reminding apparatus according to claim 10, further comprising: a motion sensor, wherein the motion sensor is connected with the controller for detecting a motion state of the tabletop of the height-adjustable table.

13. The timing reminding apparatus according to claim 10, wherein: at least one second photoelectric sensor is further provided, the second photoelectric sensor is connected with the controller, and the second photoelectric sensor and the first photoelectric sensor are respectively arranged at different positions of the height-adjustable table, and the two sensors have the same installation height.

14. The timing reminding apparatus according to claim 10, further comprising: a touch display screen used for inputting related setting information and used for displaying text reminding; wherein the reminding unit comprises a sound reminding module and/or an LED prompting lamp, and both of the sound reminding module and/or the LED prompting lamp are connected with the controller for sending sound reminding and/or LED prompting lamp flashing reminding.

15. A timing reminding apparatus for a height-adjustable table, comprising:
   a sensor combination used for detecting whether a user is in front of the height-adjustable table;
   the sensor combination comprises a pyroelectric infrared sensor and a first distance measure sensor; or
   the sensor combination comprises a pyroelectric infrared sensor and a thermal imaging sensor; or
   the sensor combination comprises a pyroelectric infrared sensor and an image identification sensor; and
   a proximity switch, a magnetic induction switch or a second distance measure sensor arranged on the height-adjustable table for judging a use posture of the user; and
   a controller used for receiving detection information of the sensor combination and the proximity switch or the magnetic induction switch, matching a reminding time according to the received information and timing.

16. The timing reminding apparatus according to claim 15, further comprising: a touch display screen used for inputting related setting information and used for displaying text reminding; and
   a reminding unit, wherein the reminding unit comprises a sound reminding module and/or an LED prompting lamp, and both of the sound reminding module and/or the LED prompting lamp are connected with the controller for sending sound reminding and/or LED prompting lamp flashing reminding.

17. The timing reminding apparatus according to claim 15, further comprising: a Bluetooth module or a wireless module for connecting with a mobile terminal or a cloud.

* * * * *

UNITED STATES PATENT AND TRADEMARK OFFICE
CERTIFICATE OF CORRECTION

PATENT NO. : 10,872,516 B2
APPLICATION NO. : 16/344265
DATED : December 22, 2020
INVENTOR(S) : Zhu et al.

It is certified that error appears in the above-identified patent and that said Letters Patent is hereby corrected as shown below:

On the Title Page

Item (22), replace "PCT Filed: Oct. 7, 2017" with --PCT Filed: Jul. 10, 2017--

Signed and Sealed this
Thirty-first Day of May, 2022

Katherine Kelly Vidal
*Director of the United States Patent and Trademark Office*